US00PP25998P3

(12) United States Plant Patent
Striem et al.

(10) Patent No.: US PP25,998 P3
(45) Date of Patent: Oct. 20, 2015

(54) GRAPEVINE PLANT NAMED 'SUGRAFORTYTHREE'

(50) Latin Name: *Vitis vinifera*
Varietal Denomination: Sugrafortythree

(71) Applicant: Sun World International, LLC, Bakersfield, CA (US)

(72) Inventors: Michael J. Striem, Rehovot (IL); Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 168 days.

(21) Appl. No.: 13/998,454

(22) Filed: Nov. 1, 2013

(65) Prior Publication Data

US 2015/0128317 P1 May 7, 2015

(51) Int. Cl.
*A01H 5/08* (2006.01)

(52) U.S. Cl.
USPC ..... Plt./207

(58) Field of Classification Search
USPC ..... Plt./207
CPC ..... A01H 5/0812; A01H 5/08
See application file for complete search history.

*Primary Examiner* — Kent L Bell
(74) *Attorney, Agent, or Firm* — Knobbe, Martens, Olson & Bear, LLP

(57) ABSTRACT

A new and distinct grapevine variety is characterized in that it produces a medium sized, broad, green ellipsoid berry with a large bunch size. The berries of 'Sugrafortythree' are firm and very juicy. The new variety 'Sugrafortythree' is characterized by a late ripening period and ripens most similarly to 'Autumn King' (U.S. Plant Pat. No. 16,284). In the Bakersfield, Calif. area the new variety 'Sugrafortythree' has a harvest start date of October 1 compared to September 15$^{th}$ for 'Autumn King'.

1 Drawing Sheet

Latin name of the genus and species claimed: *Vitis vinifera*.
Variety denomination: 'SUGRAFORTYTHREE'.

BACKGROUND AND SUMMARY OF THE INVENTION

This invention relates to the discovery and asexual propagation of a new and distinct variety of grapevine, 'Sugrafortythree', as herein described and illustrated. The new variety was first hybridized in October 2010 by Terry A. Bacon in Wasco, Kern County, Calif. The variety was originated by controlled hybridization.

The new variety 'Sugrafortythree' is characterized by a late ripening period, the production of a medium sized, green and broad ellipsoid berry with a large bunch size. The berries of 'Sugrafortythree' are firm and very juicy.

The seed parent is the varietal selection '00061-153-466' (unpatented) and the pollen parent is the varietal selection 'Sugrathirtyone' (U.S. Plant Pat. No. 19,065). The parent varieties were first crossed in May 2006 by Michael J. Striem. The date of first sowing was March 2007, and the date of first flowering was May 2010.

The new variety 'Sugrafortythree' was first asexually propagated in December 2009 in Wasco, Kern County, Calif., by Terry A. Bacon using hardwood cuttings.

The new variety 'Sugrafortythree' differs from its seed parent '00061-153-466' (unpatented) in that the new variety ripens later, starting harvest about October 1$^{st}$ compared to August 28$^{th}$ for the seed parent.

The new variety 'Sugrafortythree' differs from its pollen parent 'Sugrathirtyone' (U.S. Plant Pat. No. 19,065) in that the new variety ripens later, starting harvest about October 1$^{st}$ compared to August 23$^{rd}$ for the pollen parent.

The new variety 'Sugrafortythree' ripens most closely to 'Autumn King' (U.S. Plant Pat. No. 16,284). In the Bakersfield, Calif. area 'Autumn King' has a harvest start date of September 15$^{th}$ compared to October 1$^{st}$ for the new variety. Additionally, the new variety 'Sugrafortythree' differs from 'Autumn King' (U.S. Plant Pat. No. 16,284) in that the berry weight of the new variety is less: 8.5 g compared to 11 g for 'Autumn King' (U.S. Plant Pat. No. 16,284).

The new 'Sugrafortythree' variety has been shown to maintain its distinguishing characteristics through successive asexual propagations by, for example, cuttings.

Variations of the usual magnitude from the characteristics described herein may occur with changes in any of a variety of factors such as growing conditions, irrigation, fertilization, pruning, management and climatic variation.

BRIEF DESCRIPTION OF THE DRAWING

The accompanying color photographic illustration shows typical specimens of the foliage and fruit of the present new grape variety 'Sugrafortythree'.

The illustration shows the upper and lower surface of the leaves and exterior and sectional view of the fruit.

The photographic illustration was taken shortly after the fruit was picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England, 1986.

Many of the descriptive values in this specification are based on and conform to those set forth by the International Board for Plant Genetic Resources Institute Grape Descriptors (*Vitis* spp.) of 1983 and/or 1997, which was developed in collaboration with the Office International de la Vigne et du Vin (OIV) and the International Union for the Protection of New Varieties of Plants (UPOV).

The descriptive matter which follows pertains to 'Sugrafortythree' plants grown in the vicinity of Wasco, Kern County, Calif. during 2013, and is believed to apply to plants of the variety grown under similar conditions of soil and climate elsewhere.

VINE

General:

*Practices.*—Gene-pool-vine: Cane pruned to approximately 6 spurs per vine. Test-vines: Cane pruned to approximately 6 spurs per vine.

*Size.*—Medium. Height: Medium, Approximately 2.0 m. Width: Approximately 2.2 m.

*Vigor.*—Mildly vigorous.

*Fresh pruning weight.*—Approximately 6 kg per vine.

*Density of foliage.*—Medium.

*Productivity.*—Productive — approximately 40 clusters per vine after thinning.

*Yield.*—Approximately 32 kg per vine.

*Crop load.*—Approximately 5.3 kg per vine (kg fruit per kg fresh-pruning-weight).

*Own root.*—Yes.

*Resistance.*—Neither resistance nor susceptibility to diseases or pests has been observed in this variety.

Trunk:

*Shape.*—Circular.

*Diameter.*—Approximately 87 mm.

*Straps.*—Short.

*Surface texture.*—Shaggy.

*Inner bark color.*—Near Medium Greyed-Orange 165C.

*Outer bark color.*—Near Dark Greyed-green 197B.

SHOOTS

Young shoot:

*Form of tip.*—Half open.

*Distribution of anthocyanin coloration of tip.*—Striped.

*Intensity of anthocyanin coloration of tip.*—Weak.

*Density of prostrate hairs on tip.*—Medium.

*Density of erect hairs on tip.*—Absent.

Woody shoot (mature canes):

*Shape.*—Slender.

*Internode length.*—Approximately 170 mm.

*Width at node.*—Approximately 15 mm.

*Cross section.*—Circular.

*Surface.*—Smooth.

*Main color.*—About Medium Greyed-Orange 165C.

*Lenticels.*—Absent.

*Density of erect hairs on nodes.*—Absent or Very Sparse.

*Density of erect hairs on internodes.*—Absent or Very Sparse.

*Growth of auxiliary shoots.*—Average 16.5 cm/shoot.

Flowering shoot:

*Vigor during flowering.*—Medium.

*Attitude during flowering on shoots which are not tied.*—Semi-erect.

*Color of dorsal side of internodes.*—About Light Green 139D and Medium Greyed-purple 165B.

*Color of ventral side of internodes.*—About Light Green 139D and Medium Greyed-purple 165B.

*Color of dorsal side of nodes.*—About Light Green 139D and Medium Greyed-purple 165B.

*Color of ventral side of nodes.*—About Light Green 139D and Medium Greyed-purple 165B.

*Density of erect hairs on nodes.*—Absent.

*Erect hairs on internode.*—Absent.

*Density of prostrate hairs on nodes.*—Absent.

*Density of prostrate hairs on internodes.*—Absent.

*Anthocyanin coloration of buds.*—Absent.

Tendrils:

*Distribution on the shoot at full flowering.*—Discontinuous.

*Thickness.*—Medium.

*Color.*—Near Medium Yellow-Green 144C.

*Form.*—Bifurcated.

*Number of consecutive tendrils.*—Up to 2.

*Length of tendril.*—Medium, approximately 14 cm.

LEAVES

Young leaves:

*Color of upper surface of first* 4 *distal unfolded leaves.*—About Light Green 139C.

*Average intensity of anthocyanin coloration of six distal leaves prior to flowering.*—Absent.

*Density of prostrate hairs between veins at lower surface of* 4*th distal unfolded leaf.*—Absent.

*Density of erect hairs between veins at lower surface of* 4*th distal unfolded leaf.*—Absent.

*Density of prostrate hairs on veins at lower surface of* 4*th distal unfolded leaf.*—Absent.

*Density of erect hairs on veins at lower surface of* 4*th distal unfolded leaf.*—Absent.

Mature leaves:

*Average length.*—Approximately 124 mm from ending of petiole to tip of leaf.

*Average width.*—Approximately 140 mm.

*Size of blade.*—Medium.

*Shape of blade.*—Pentagonal.

*Number of lobes.*—Approximately 5.

*Anthocyanin coloration of main veins on the upper side of the blade.*—Absent or very faint.

*Mature leaf profile.*—Flat.

*Blistering surface of blade upper surface.*—Absent.

*Leaf blade tip.*—In the plane of the leaf.

*Undulation of margin.*—Slight.

*Thickness.*—Medium.

*Undulation of blade between main and lateral veins.*—Absent.

*Shape of teeth.*—Serrated.

*Length of teeth.*—Medium, usually 3 mm to 8 mm, average about 5 mm.

*Ratio length/width of teeth.*—Small.

*General shape of petiole sinus.*—U-shaped.

*Tooth at petiole sinus.*—Absent.

*Petiole sinus limited by veins.*—Absent.

*Shape of upper lateral sinus.*—Open.

*Depth of upper lateral sinus.*—Very Shallow.

*Density of prostrate hairs between veins on lower surface of blade.*—Absent.

*Density of erect hairs between veins on lower surface of blade.*—Absent.

*Density of prostrate hairs on main veins on lower surface of blade.*—Absent.
*Density of erect hairs on main veins on lower surface of blade.*—Absent.
*Density of prostrate hairs on main veins on upper surface of blade.*—Absent.
*Autumn coloration of leaves.*—Varies by year, About Medium Yellow-green, about 153D, to Medium Greyed-yellow, about 162A.

Upper surface:
*Color.*—About Dark Green 135B.
*Surface texture.*—Smooth.
*Surface appearance.*—Semi-glossy.
*Glossiness.*—Weak.
*Pubescence.*—Absent.

Lower surface:
*Color.*—About Medium Green 135C.
*Anthocyanin coloration of main veins on lower leaf surface.*—Absent.
*Glossiness.*—Weak.
*Pubescence.*—Absent.
*Surface texture.*—Smooth.
*Surface appearance.*—Dull.

Petiole:
*Length of petiole.*—Medium, Approximately 35 cm.
*Length of petiole compared to middle vein.*—Shorter.
*Diameter.*—Approximately 3 mm.
*Density of prostrate hairs on petiole.*—Absent.
*Density of erect hairs on petiole.*—Absent.
*Shape of base of petiole sinus.*—U-shaped.
*Color.*—About Medium Yellow-Green 144C and Medium Greyed-Red 179B.

Buds:
*Shape.*—Conical.
*Size.*—Medium, approximately 3 mm×4 mm.
*Position.*—Slightly held out.
*Cane bud fruitfulness.*—Basal most fruitful, $4^{th}$ to $5^{th}$ bud position.
*Time of bud burst.*—Medium, about March 10.

FLOWERS

General:
*Flower sex.*—Hermaphrodite.
*Sexual organs.*—Fully developed stamens and fully developed gynoecium.
*Length of first inflorescence.*—Medium, about 12 cm.
*Position of first flowering node.*—Fourth node.
*Number of inflorescences per shoot.*—Approximately 1 to 2.
*Date of full bloom.*—Approximately May 10th.
*Size (diameter of fully open flower).*—Medium, approximately 6 mm.

FRUIT

General:
*Ripening period.*—Late starting about October 1st with mid-ripe October 15.
*Use.*—Table grape fresh consumption.
*Keeping quality.*—Good.
*Shipping quality.*—Good.
*Date of first harvest.*—Approximately October $1^{st}$.
*Solids-sugar.*—High, about 20%.
*Refractometer test.*—Approximately 20%.
*Acid.*—Medium, approximately 0.60 gr./L tartaric acid.
*Juice pH.*—Approximately 3.5.
*Tendency to crack.*—Very low.
*Sensitivity to sunburn.*—Low.
*Fruit shrivel after ripe.*—Absent.
*Secondary cluster.*—Occasional.
*Resistance.*—Absent.

Cluster:
*Bunch size (peduncle excluded).*—Large.
*Bunch length (peduncle excluded).*—Medium, approximately 24 cm.
*Bunch width.*—Approximately 15 cm.
*Bunch weight.*—High, approximately 800 g.
*Bunch density.*—Medium.
*Number of berries.*—Approximately 95.
*Form.*—Africa-shaped.

Peduncle:
*Length of peduncle.*—Medium, approximately 40 mm.
*Lignification of peduncle.*—Absent.
*Color.*—About Medium Yellow-green 144A.

Berry:
*Size.*—Medium.
*Uniformity of size.*—Marginally variable.
*Berry weight.*—Medium, approximately 8.5 gr. treated.
*Gibberellic acid treated.*—Medium, 10 ppm to 20 ppm.
*Shape.*—Broad ellipsoid.
*Presence of seeds.*—Rudimentary.
*Cross section.*—Round.
*Dimensions.*—Longitudinal axis: Approximately 28 mm treated. Horizontal axis: Approximately 23 mm treated.
*Skin color (without bloom).*—About Medium Yellow-green 144D.
*Flesh color.*—About Medium Yellow-green 144C.
*Juiciness of flesh.*—Very juicy.
*Berry firmness.*—Firm.
*Particular flavor.*—None.
*Bloom (cuticular wax).*—Weak.
*Pedicel length.*—Medium approximately 10 mm.
*Berry separation from pedicel.*—Medium.
*Anthocyanin coloration of flesh.*—Absent or very weak.
*Visibility of hilum.*—Slightly.

Skin:
*Thickness.*—Medium.
*Texture.*—Smooth.
*Reticulation.*—Absent or very slight.
*Roughness.*—Absent.
*Tenacity.*—Tenacious to flesh.

Seed:
*Number of seeds per berry.*—Usually 1, sometimes 2.
*Size.*—Small.
*Color.*—About Medium Green 144B.
*Texture.*—Soft.
*Endosperm.*—Slight.
*Fresh weight of seed-traces/berry.*—Approximately 16.5 mg.
*Room-dry weight of seed-traces/berry.*—Approximately 4.1 mg.

What is claimed is:

1. A new and distinct variety of grapevine plant as herein illustrated and described.

* * * * *

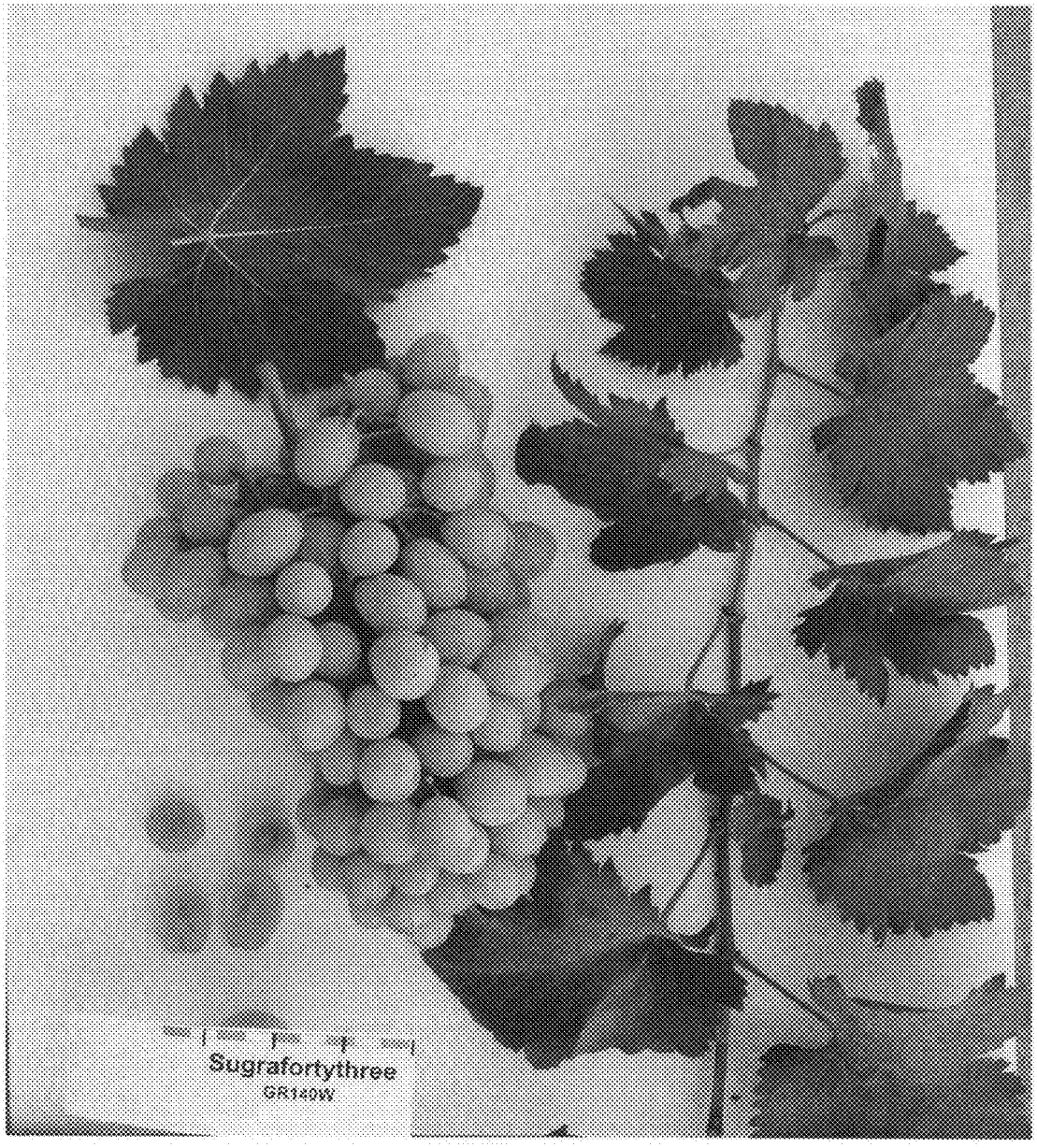
Sugrafortythree
GR140W